US012560585B2

(12) United States Patent
Al-Ani

(10) Patent No.: US 12,560,585 B2
(45) Date of Patent: Feb. 24, 2026

(54) HAZARDOUS MATERIAL DETECTING DEVICES AND COMPOSITIONS

(71) Applicant: Ma'An Nassar Raja Al-Ani, Orlando, FL (US)

(72) Inventor: Ma'An Nassar Raja Al-Ani, Orlando, FL (US)

( * ) Notice: Subject to any disclaimer, the term of this patent is extended or adjusted under 35 U.S.C. 154(b) by 334 days.

(21) Appl. No.: 18/118,060

(22) Filed: Mar. 6, 2023

(65) Prior Publication Data

US 2024/0302342 A1     Sep. 12, 2024

(51) Int. Cl.
G01N 33/18          (2006.01)

(52) U.S. Cl.
CPC ..................................... G01N 33/18 (2013.01)

(58) Field of Classification Search
CPC .... G01N 33/18; G01N 33/2888; G01N 11/00; G01N 2291/02818; G01N 29/022; G01N 29/036; G01N 2291/0256; G01N 11/16; G01N 33/1886; G01N 13/02; G01N 33/2823; G01N 33/28; G01N 13/00; G01N 11/14; G01N 2291/0423; G01N 29/222; G01N 11/08; G01N 29/024; G01N 33/4905; G01N 2991/0427; G01N 29/032; G01N 11/06; G01N 9/36; G01N 2291/0226; G01N 2001/4016; G01N 1/405; G01N 15/04; G01N 21/78; G01N 33/0031; G01N 33/2847; G01N 35/08; G01N 27/221; G01N 33/442; G01N 7/14; G01N 21/05; G01N 2291/02836; G01N 2291/02881; G01N 2291/0422; G01N 2291/0426; G01N 29/348; G01N 29/46;

G01N 33/30; G01N 1/34; G01N 15/02; G01N 2001/021; G01N 2015/0092; G01N 21/8483; G01N 2291/014; G01N 2291/02416;

(Continued)

(56) References Cited

U.S. PATENT DOCUMENTS

| | | | |
|---|---|---|---|
| 6,941,806 B2 * | 9/2005 | Burns | ................ G01N 33/0075 |
| | | | 73/170.01 |
| 10,186,135 B2 * | 1/2019 | Trubey | ............... G01N 33/0062 |
| 10,604,729 B2 | 3/2020 | Hawkins et al. | |
| 2004/0020422 A1 * | 2/2004 | Tsengas | ................ G01N 31/22 |
| | | | 116/206 |

(Continued)

FOREIGN PATENT DOCUMENTS

| | | | |
|---|---|---|---|
| BG | 67405 B1 | * | 12/2021 |
| CN | 203960207 U | | 11/2014 |

(Continued)

OTHER PUBLICATIONS

"Wireless Gas Detectors With Wireless Control Unit," Copyright @ 2019 Ambetronics Engineers Pvt.Ltd.: https://ambetronics.com/home/gas-detection-systems/wireless_gas_detectors/.

*Primary Examiner* — Andre J Allen
(74) *Attorney, Agent, or Firm* — Nath, Goldberg & Meyer; Joshua B. Goldberg

(57)                    ABSTRACT
A toxic material detecting device includes an outer casing and a toxic material retaining composition within the casing. The toxic material detecting device can detect the presence of radioactive, chemical, biological, and toxic materials in air, gases, oils, soil, and water that contact one or more detection chambers within the device. The toxic material retaining composition can retain the toxic material within the device for a period of time sufficient for detection, thereby providing increased sensitivity for the device.

18 Claims, 14 Drawing Sheets

(58) Field of Classification Search

CPC .... G01N 25/18; G01N 33/0009; G01N 33/32; G01N 15/06; G01N 2013/0208; G01N 2291/0224; G01N 2291/0255; G01N 29/30; G01N 33/15; G01N 33/2858; G01N 33/44; G01N 35/1016; G01N 9/00; G01N 15/0656; G01N 2013/003; G01N 2203/0094; G01N 2291/106; G01N 29/02; G01N 33/2829; G01N 7/00; G01N 9/002; G01N 1/38; G01N 11/02; G01N 15/0205; G01N 17/00; G01N 2001/4066; G01N 2291/0222; G01N 25/147; G01N 29/4427; G01N 30/32; G01N 30/34; G01N 33/1826; G01N 33/2852; G01N 33/2876; G01N 33/383; G01N 1/12; G01N 11/10; G01N 2013/006; G01N 2013/0283; G01N 2021/0346; G01N 2035/00158; G01N 22/00; G01N 2291/0258; G01N 2291/02809; G01N 25/14; G01N 27/223; G01N 33/4925; G01N 35/0098; G01N 35/0099; G01N 1/10; G01N 1/4044; G01N 15/12; G01N 2015/0096; G01N 2035/00237; G01N 2035/00247; G01N 21/15; G01N 2291/044; G01N 25/02; G01N 27/126; G01N 27/226; G01N 27/44791; G01N 30/6095; G01N 33/0006; G01N 33/1893; G01N 33/22; G01N 33/48785; G01N 35/1095; G01N 7/10; G01N 9/24; G01N 1/14; G01N 1/2035; G01N 1/24; G01N 1/28; G01N 11/04; G01N 15/0227; G01N 19/02; G01N 2015/0038; G01N 21/03; G01N 21/0303; G01N 21/0332; G01N 21/3577; G01N 21/8507; G01N 2291/02863; G01N 27/021; G01N 27/06; G01N 3/56; G01N 30/88; G01N 33/1806; G01N 33/24; G01N 33/2835; G01N 33/287; G01N 33/4875; G01N 35/00; G01N 35/00594; G01N 35/00693; G01N 35/00871; G01N 5/02; G01N 1/40; G01N 1/4077; G01N 13/04; G01N 15/042; G01N 15/1459; G01N 2013/0275; G01N 2015/0053; G01N 2030/008; G01N 2030/025; G01N 21/648; G01N 21/85; G01N 22/04; G01N 2203/0066; G01N 2203/024; G01N 2203/0246; G01N 2291/011; G01N 2291/02433; G01N 25/08; G01N 27/026; G01N 27/127; G01N 27/286; G01N 27/403; G01N 27/4165; G01N 27/4166; G01N 27/44743; G01N 27/74; G01N 29/42; G01N 3/08; G01N 30/62; G01N 33/0073; G01N 33/0091; G01N 33/03; G01N 33/146; G01N 33/1833; G01N 33/26; G01N 33/5302; G01N 33/5438; G01N 9/26; G01N 2011/008; G01N 2015/1024; G01N 2030/062; G01N 2030/326; G01N 2035/00554; G01N 2035/00752; G01N 21/293; G01N 2203/0023; G01N 2203/0092; G01N 2291/017; G01N 2291/0215; G01N 2291/101; G01N 27/4163; G01N 33/00; G01N 30/16; G01N 31/22; G01N 33/0011; G01N 33/487; G01N 33/54373; G01N 35/00712; G01N 1/16; G01N 1/22; G01N 1/2214; G01N 1/2247; G01N 1/2273; G01N 15/0266; G01N 15/05; G01N 15/065; G01N 17/002; G01N 19/10; G01N 2009/006; G01N 2013/0225; G01N 2013/0241; G01N 2015/0288; G01N 2015/045; G01N 2015/0687; G01N 2015/1486; G01N 2021/054; G01N 2021/152; G01N 2021/3595; G01N 2021/6439; G01N 2030/128; G01N 2030/204; G01N 2030/324; G01N 2030/342; G01N 2035/00683; G01N 2035/1032; G01N 2035/1044; G01N 2035/1062; G01N 21/33; G01N 21/53; G01N 21/64; G01N 21/6428; G01N 21/6486; G01N 21/65; G01N 21/7703; G01N 21/91; G01N 2203/0085; G01N 2203/027; G01N 2223/076; G01N 2291/02845; G01N 2291/02872; G01N 2291/0421; G01N 2291/102; G01N 23/223; G01N 27/04; G01N 27/128; G01N 27/18; G01N 27/22; G01N 27/307; G01N 27/3272; G01N 27/3273; G01N 27/3275; G01N 27/38; G01N 27/4145; G01N 27/416; G01N 27/447; G01N 27/30; G01N 27/745; G01N 29/14; G01N 29/2462; G01N 29/2481; G01N 29/343; G01N 29/4436; G01N 29/4481; G01N 3/02; G01N 3/40; G01N 30/00; G01N 30/02; G01N 30/12; G01N 30/20; G01N 30/463; G01N 30/8675; G01N 31/222; G01N 33/0016; G01N 33/0034; G01N 33/02; G01N 33/14; G01N 33/205; G01N 33/241; G01N 33/2805; G01N 33/2811; G01N 33/2817; G01N 33/48707; G01N 33/48757; G01N 33/49; G01N 33/4915; G01N 33/493; G01N 33/497; G01N 33/528; G01N 33/54386; G01N 33/80; G01N 33/84; G01N 33/92; G01N 35/028; G01N 35/085; G01N 35/10; G01N 5/00; G01N 9/04; G01N 9/32; G01N 1/2202; G01N 1/2208; G01N 15/082; G01N 15/1456; G01N 15/149; G01N 17/008; G01N 2001/2057; G01N 2001/2064; G01N 2001/2223; G01N 2001/2267; G01N 2001/4027; G01N 2001/4088; G01N 2011/0046; G01N 2011/006; G01N 2011/0066; G01N 2015/0675; G01N 2015/1006; G01N 2015/1029; G01N 2021/0325; G01N 2021/0382; G01N 2030/065; G01N 2035/00217; G01N 2035/00524; G01N 2035/00534; G01N 2035/1018; G01N 21/3504; G01N 21/359; G01N 21/82; G01N 2203/0284; G01N 2203/0286; G01N 2203/0623; G01N 2203/0682; G01N 2291/0253; G01N 2291/0254; G01N 27/00; G01N 27/02; G01N 27/07; G01N 27/10; G01N 27/121; G01N 27/122; G01N 27/3271; G01N 27/36; G01N 2800/52; G01N 29/11; G01N 3/32; G01N 30/0005; G01N 30/06; G01N 30/64; G01N 30/7206; G01N 30/8658; G01N 31/00; G01N 33/0047; G01N 33/1846; G01N 33/188; G01N 33/48; G01N 33/50; G01N 33/5005; G01N 33/52; G01N 33/54306;

G01N 33/54388; G01N 33/54393; G01N 35/026; G01N 35/04; G01N 35/1097; G01N 37/005; G01N 9/12; G01N 1/00; G01N 1/04; G01N 1/2042; G01N 1/2205; G01N 1/26; G01N 1/30; G01N 1/312; G01N 1/36; G01N 1/4005; G01N 1/4022; G01N 1/44; G01N 11/167; G01N 15/00; G01N 15/0272; G01N 15/0625; G01N 15/0631; G01N 15/075; G01N 15/0826; G01N 15/088; G01N 15/0893; G01N 15/1031; G01N 15/14; G01N 15/1404; G01N 15/1434; G01N 15/147; G01N 15/1484; G01N 17/006; G01N 17/046; G01N 2001/022; G01N 2001/1093; G01N 2001/1427; G01N 2001/2217; G01N 2001/2232; G01N 2001/2282; G01N 2001/4011; G01N 2011/004; G01N 2011/0073; G01N 2011/0093; G01N 2013/025; G01N 2015/0011; G01N 2015/012; G01N 2015/0233; G01N 2015/035; G01N 2015/0668; G01N 2015/084; G01N 2015/0866; G01N 2015/1022; G01N 2015/1027; G01N 2015/103; G01N 2015/144; G01N 2015/145; G01N 2015/1493; G01N 2021/258; G01N 2021/6478; G01N 2021/6482; G01N 2021/6484; G01N 2021/772; G01N 2021/8477; G01N 2030/009; G01N 2030/121; G01N 2030/146; G01N 2030/201; G01N 2030/207; G01N 2030/3007; G01N 2030/328; G01N 2030/347; G01N 2030/521; G01N 2030/565; G01N 2030/625; G01N 2030/645; G01N 2030/746; G01N 2030/765; G01N 2030/8447; G01N 2030/8804; G01N 2030/8809; G01N 2030/8813; G01N 2030/8831; G01N 2030/885; G01N 2030/8854; G01N 2030/8881; G01N 2035/00089; G01N 2035/00198; G01N 2035/00326; G01N 2035/00574; G01N 2035/0425; G01N 2035/1034; G01N 2035/1046; G01N 21/23; G01N 21/29; G01N 21/31; G01N 21/3103; G01N 21/4133; G01N 21/532; G01N 21/552; G01N 21/554; G01N 21/643; G01N 21/6445; G01N 21/645; G01N 21/6454; G01N 21/6458; G01N 21/68; G01N 21/76; G01N 21/7743; G01N 21/79; G01N 21/81; G01N 21/84; G01N 21/93; G01N 21/94; G01N 2201/0218; G01N 2201/0227; G01N 2201/024; G01N 2201/061; G01N 2203/025; G01N 2203/0226; G01N 2203/0232; G01N 2203/0256; G01N 2203/0296; G01N 2203/0676; G01N 2203/0688; G01N 2291/02408; G01N 2291/02466; G01N 2291/056; G01N 2291/103; G01N 2291/2698; G01N 23/125; G01N 23/20; G01N 23/203; G01N 2333/575; G01N 2333/62; G01N 2333/75; G01N 2333/90209; G01N 2446/00; G01N 2458/00; G01N 25/00; G01N 25/085; G01N 25/12; G01N 25/48; G01N 25/52; G01N 25/66; G01N 2570/00; G01N

2600/00; G01N 27/023; G01N 27/025; G01N 27/125; G01N 27/27; G01N 27/28; G01N 27/302; G01N 27/305; G01N 27/327; G01N 27/3276; G01N 27/401; G01N 27/414; G01N 27/4143; G01N 27/4162; G01N 27/4167; G01N 27/423; G01N 27/44726; G01N 27/44752; G01N 27/44756; G01N 27/62; G01N 27/70; G01N 27/72; G01N 2800/042; G01N 2800/122; G01N 2800/28; G01N 2800/32; G01N 29/041; G01N 29/2412; G01N 29/345; G01N 29/38; G01N 3/12; G01N 3/18; G01N 3/20; G01N 3/24; G01N 30/10; G01N 30/24; G01N 30/36; G01N 30/466; G01N 30/52; G01N 30/56; G01N 30/6026; G01N 30/6034; G01N 30/6086; G01N 30/6091; G01N 30/66; G01N 30/72; G01N 30/7233; G01N 30/74; G01N 30/76; G01N 30/84; G01N 30/8651; G01N 30/8665; G01N 30/8679; G01N 30/96; G01N 31/16; G01N 31/221; G01N 33/0001; G01N 33/0004; G01N 33/0013; G01N 33/0014; G01N 33/0037; G01N 33/004; G01N 33/0044; G01N 33/0049; G01N 33/0075; G01N 33/025; G01N 33/04; G01N 33/08; G01N 33/1813; G01N 33/182; G01N 33/186; G01N 33/1866; G01N 33/225; G01N 33/246; G01N 33/2841; G01N 33/34; G01N 33/343; G01N 33/36; G01N 33/42; G01N 33/483; G01N 33/48714; G01N 33/48771; G01N 33/491; G01N 33/492; G01N 33/5029; G01N 33/5091; G01N 33/5097; G01N 33/521; G01N 33/5308; G01N 33/54326; G01N 33/558; G01N 33/56938; G01N 33/582; G01N 33/66; G01N 33/6812; G01N 33/6839; G01N 33/6842; G01N 33/6854; G01N 33/6872; G01N 33/6893; G01N 33/6896; G01N 33/74; G01N 33/743; G01N 33/86; G01N 33/94; G01N 35/00029; G01N 35/00069; G01N 35/02; G01N 35/021; G01N 35/025; G01N 35/1002; G01N 35/1011; G01N 35/1074; G01N 9/08; G01N 9/14; G01N 9/18; G01N 9/28; G01N 1/02; G01N 1/08; G01N 1/20; G01N 1/2294; G01N 11/12; G01N 11/162; G01N 15/01; G01N 15/0606; G01N 15/0618; G01N 15/10; G01N 15/13; G01N 19/04; G01N 2001/028; G01N 2001/1025; G01N 2001/2276; G01N 2015/0046; G01N 2015/016; G01N 2015/1016; G01N 2015/1028; G01N 15/135; G01N 2021/1704; G01N 2021/8528; G01N 2021/8557; G01N 2030/027; G01N 2030/3084; G01N 2035/00188; G01N 2023/00495; G01N 2035/00881; G01N 2035/0403; G01N 2035/0406; G01N 2035/0412; G01N 2035/0441; G01N 2035/1006; G01N 2035/1025; G01N 21/1702; G01N 21/251; G01N 21/253; G01N 21/272; G01N 21/274; G01N 21/37; G01N 21/59; G01N 21/6447; G01N 21/77; G01N 2201/128; G01N 2203/0617; G01N 2291/012; G01N

2291/0217; G01N 2291/0257; G01N
2291/2634; G01N 2500/00; G01N 27/26;
G01N 27/4175; G01N 27/44704; G01N
27/622; G01N 2800/54; G01N 29/043;
G01N 29/045; G01N 29/223; G01N
29/228; G01N 29/4472; G01N 30/28;
G01N 30/30; G01N 30/54; G01N 30/86;
G01N 33/0022; G01N 33/0026; G01N
33/0032; G01N 33/0095; G01N 33/1853;
G01N 33/20; G01N 33/208; G01N
33/2894; G01N 33/5008; G01N 33/53;
G01N 33/5306; G01N 33/54353; G01N
33/54366; G01N 33/5748; G01N
35/00732; G01N 35/1009; G01N 37/00;
G01N 5/04

USPC ......................................................... 73/53.01

See application file for complete search history.

(56)                   References Cited

U.S. PATENT DOCUMENTS

| 2017/0026723 | A1 | 1/2017 | Wan et al. | |
| 2017/0261468 | A1 | 9/2017 | Chan et al. | |
| 2022/0412947 | A1* | 12/2022 | Javanmard | G01N 1/4044 |
| 2024/0426806 | A1* | 12/2024 | Liu | C12Q 1/04 |

FOREIGN PATENT DOCUMENTS

| CN | 105738439 | A | 7/2016 |
| CN | 105891263 | A | 8/2016 |
| CN | 108956724 | A | 12/2018 |
| DE | 2416828 | A1 | 10/1975 |
| KR | 20190012046 | A | 2/2019 |

* cited by examiner

302

700

702

704

702

706

702

800

700

9

9

804

804

802

704

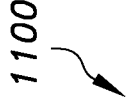

*1100*

1114
VCC
TX/Out
SCL
BME680 Arduino Gas Sensor
SDA
GND
P4

1116
VCC
TX/Out
PLM35: Analog Temperature Sensor
SCL
SDA
GND
P5

1118
VCC
TX/Out
Alpha: Radiation Sensor
SCL
SDA
GND
P6

1102
5V
D13
D12
D11
D10
D9
D7
D6
D5
D4
D3
D2
TXDD1
RXDDO
GND
A0
A1
A2
A3
A4/SDA
A5/SCL

1104
VCC
SCL
IN
SDA
S1
S2
S3
EN
GND
SCL P8 SDA
SCL P7 SDA
SCL P1 SDA
SCL P2 SDA
SCL P3 SDA
SCL P4 SDA
SCL P5 SDA
SCL P6 SDA

1106
VCC
Radiation Sensor AG X100-7
TX/OUT
P1
SDA  SCL  GND

1108
GND
PH-Sensor
P2
VCC
TX/OUT
SCL
SDA

1110
GND
SCL
SDA
CMOS Sensor
VDD
P3
TX/OUT

1112
GND
TXD
RXD
HC-05 Bluetooth
VCC

HAZARDOUS MATERIAL DETECTING DEVICES AND COMPOSITIONS

BACKGROUND

1. Field

The disclosure of the present patent application relates to toxic material detection, and particularly to toxic material detecting devices and compositions.

2. Description of the Related Art

Nuclear and biological accidents initiated through natural disturbances, war, human error, terror attack, misuse of radioactive materials in industrial applications (e.g., coal-fired power plants, and naturally occurring radioactive material (NORM) from oil and gas drilling), and nuclear and biomedical research (e.g., artificial radionuclides) can release radioactive material, microorganisms, and viruses into the air, land, and water. As release of these toxic materials can be detrimental to life, a mechanism for detecting and eliminating toxic materials from the environment is desperately needed.

Conventional devices for detecting radioactive, chemical, biological, and toxic materials have been somewhat limited in their detection sensitivity. For example, many of these detection devices do not detect small quantities of toxic materials if their residence time is insufficient within or near the detection devices. Conventional compositions that are used in conjunction with these devices are also limited in their ability to adsorb and retain the toxic materials long enough to be detected.

Thus, a toxic material detecting device solving the aforementioned problems is desired.

SUMMARY

A toxic material detecting device includes an outer casing and a toxic material retaining composition within the casing. The toxic material detecting device can detect the presence of radioactive, chemical, biological, and toxic materials in air, gases, oils, soil, and water that contact one or more detection chambers within the device. The toxic material retaining composition can retain the toxic material within the device for a period of time sufficient for detection, thereby providing increased sensitivity for the device.

A first embodiment of a toxic material detecting device can be useful for detecting toxic material prevalent in hydrosphere locations and includes an outer hollow casing. The casing can be in the shape of a sphere or ovoid. In an embodiment, the device can be buoyant, e.g., capable of floating on the top of a liquid. In an embodiment, the device can operate submerged within soil or water. The device can be heat resistant and can withstand extremely low temperatures. The casing includes an upper casing half and a lower casing half. A hollow, perforated toroid with a central opening extends between the upper and lower casing. A desired material for testing can enter the casing through perforations defined within a toroid wall. The upper casing houses an upper material detecting component. The lower casing houses a lower material detecting component. A detecting station is disposed within the central opening of the toroid.

The upper material detecting component can include a first hollow spherical chamber, a second hollow spherical chamber, a third hollow spherical chamber and a material distribution pipe extending through the first, second, and third hollow spherical chambers. The material distribution pipe includes a central longitudinal bore and a plurality of perforations in a peripheral wall through which material may enter and exit the spherical chambers. The first spherical chamber can include an aluminum shell with a first sensor mounted on an inner surface thereof. First sensor wires connect the first sensor to the detecting station. The second spherical chamber can include an aluminum shell coated with graphene. The second spherical shell can have a second sensor mounted on an inner surface thereof. Second sensor wires connect the second sensor to the detecting station. The third spherical chamber can include a clay shell with a third sensor mounted on an inner surface thereof. Preferably, the clay is Ramadi clay, or clay including about 69-72% clay and about 20-25% silt. The clay can include 70% sodium montmorillonite (Na, Ca)$_{0.33}$(Al, Mg)$_2$(Si$_4$O$_{10}$) (OH)$_2$ nH$_2$O). The Ramadi clay can be obtained from Ramadi City, Iraq. Third sensor wires connect the third sensor to the detecting station. Each of the first, second, and third hollow spherical chambers include a toxic material retaining composition for retaining a toxic material passing into the respective chamber for a duration sufficient to be detected by the respective sensors. The sensors may be gamma radiation, pH, CMOS, gas, temperature, or alpha radiation sensors.

The lower material detecting component includes an inner clay cylinder and an outer graphene netting. The inner clay cylinder includes a plurality of holes in a peripheral wall thereof and a central blind bore. A fourth sensor is mounted on an inner surface of the peripheral wall and sensor wires extend through one of the holes. A toxic material detecting composition can be included at the bottom of the bore. The fourth sensor may be a radiation, pH, CMOS, gas, temperature, or alpha radiation sensor.

The detecting station includes a wire support shell, one or more printed circuit boards (PCBs), and a waterproof container for housing the support shell. An upper half of the waterproof container and a lower half of the waterproof container are sealed together with the PCB therein, to protect the PCB from the material or fluids to be tested. A wiring harness connects the PCB to the various sensors and includes the individual sensor wires. The circuit of the PCB(s) includes a microcontroller (with memory), and an analog multiplexor. An optional communication module, such as a Bluetooth or Wi-Fi module, may be used, or the data may be stored in the memory of the microcontroller and downloaded when the material detecting device is retrieved. The power for the various components can be provided by a rechargeable battery housed within the waterproof container.

A second embodiment of a toxic material detecting device includes a lower main chamber and an upper chamber and latches for sealing the upper chamber to the lower chamber. A lid is attached to the open top of the upper chamber by a hinge and a latch is provided to maintain the lid in a closed position. An electrical input connector is connected to an electrical source for powering the internal components. An input pipe extending into the interior of the upper chamber, a material distribution pipe, and a thermometer extend through openings in the lid. This embodiment of the material detecting device is connected to external distillation equipment by a condenser supply pipe that extends through a hole in the sidewall of the upper chamber and through a cooling jacket. A chiller supplies cold coolant to the cooling jacket, via a cold coolant supply pipe, and receives warm coolant from the cooling jacket, via a warm coolant return line. Condensate from the condenser supply pipe is received in a condensate vessel. The input pipe is connected to an inlet plenum, with a bottom wall having a plurality of perforations for distributing the material being tested into the interior of the material detecting device. The material distribution pipe is part of a material detection component described below. The thermometer includes a temperature probe and wires, for connecting the thermometer to a microcontroller of the material detecting device. A condenser supply assembly includes a thermometer probe port at the top end of a device outlet pipe. The condenser supply pipe extends downwardly from the device outlet pipe. An outlet plenum supplies testing material to the device outlet pipe. The bottom wall of the outlet plenum includes a plurality of perforations through which the testing material may pass. A waterproof circuit board housing is located at the bottom of the device and houses a PCB such as the PCB described with respect to the first embodiment of the material detecting device. A sensor is located near the bottom of the device, and is attached to a sidewall of a Ramadi clay vessel or liner that is inserted into the lower chamber. The sensor is attached to the PCB via the wiring harness. The lower main chamber may be heated by an external or internal heater, thereby forming a clay-lined oven.

The material detection component includes the material distribution pipe, a first hollow frustoconical chamber, a second hollow frustoconical chamber, and a third hollow frustoconical chamber. The material distribution pipe includes a central longitudinal bore and a plurality of perforations in a peripheral wall thereof for allowing material to pass into the frustoconical chambers. The first frustoconical chamber includes an aluminum shell with a first sensor mounted on an inner surface thereof. First sensor wires connect the first sensor to the PCB in the waterproof circuit board housing. The second frustoconical chamber includes an aluminum shell covered by graphene. The aluminum shell has a second sensor mounted on an inner surface thereof. Second sensor wires connect the second sensor to the PCB in the waterproof circuit board housing. The third frustoconical chamber includes a Ramadi clay shell with a third sensor mounted on an inner surface thereof. Third sensor wires connect the third sensor to the PCB in the waterproof circuit board housing. The interior of each of the frustoconical chambers further includes the toxic material retaining composition. The sensors of both material detecting devices may be radiation, pH, CMOS, gas, temperature, or alpha radiation sensors.

The toxic material retaining composition is a montmorillonite/poly(vinyl alcohol) (MMT/PVA) zeolite/activated charcoal composite with the hierarchical shape of MMT-MMT-PVA-MMT-NZC-MMT, with cocamidopropyl betaine (CAPB) positioned between the central portions of the MMT layers and sodium lauryl ether sulfate (SLES) positioned between the edge portions of the MMT layers. The composition is highly adsorbent and has high porosity. The composition can absorb toxins, chemicals and heavy metals.

These and other features of the present subject matter will become readily apparent upon further review of the following specification.

BRIEF DESCRIPTION OF THE DRAWINGS

FIG. 11 is a circuit diagram of a circuit board of the centrally located signal processing and communication station of FIG. 10.

Similar reference characters denote corresponding features consistently throughout the attached drawings.

DETAILED DESCRIPTION OF THE PREFERRED EMBODIMENTS

Figure 1:
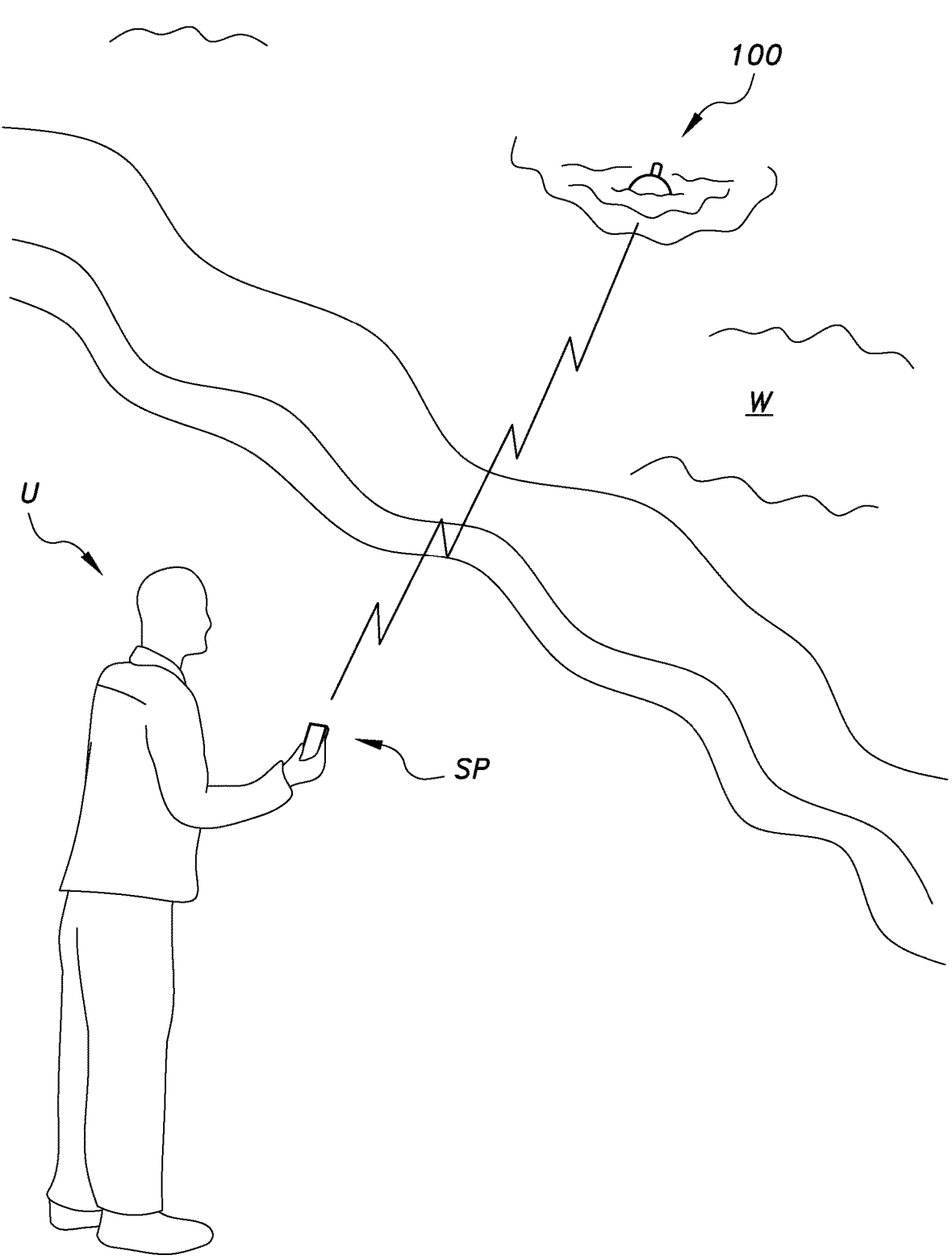
FIG. 1 is an environmental perspective view of a first embodiment of a toxic material detecting device, shown floating on a body of water.
Figure 2:
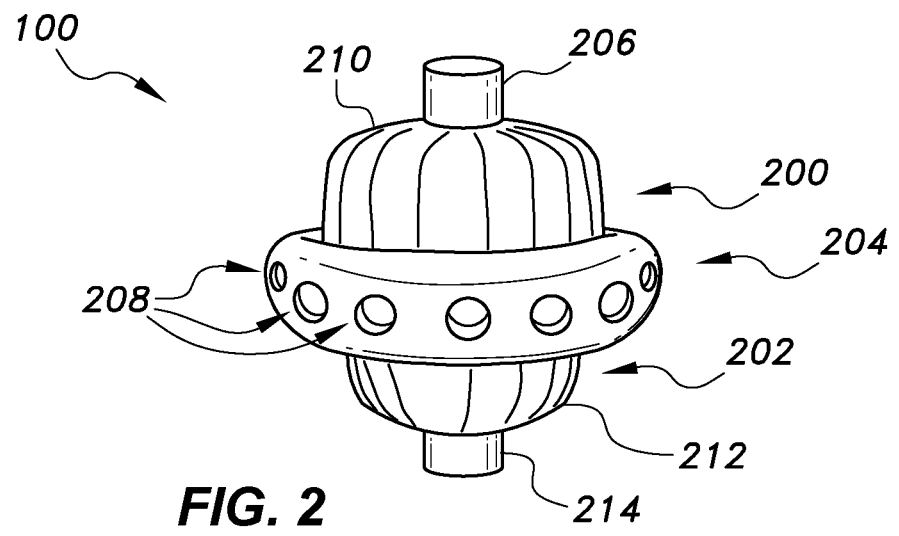
FIG. 2 is a side view of the material detecting device of FIG. 1.
Figure 3:
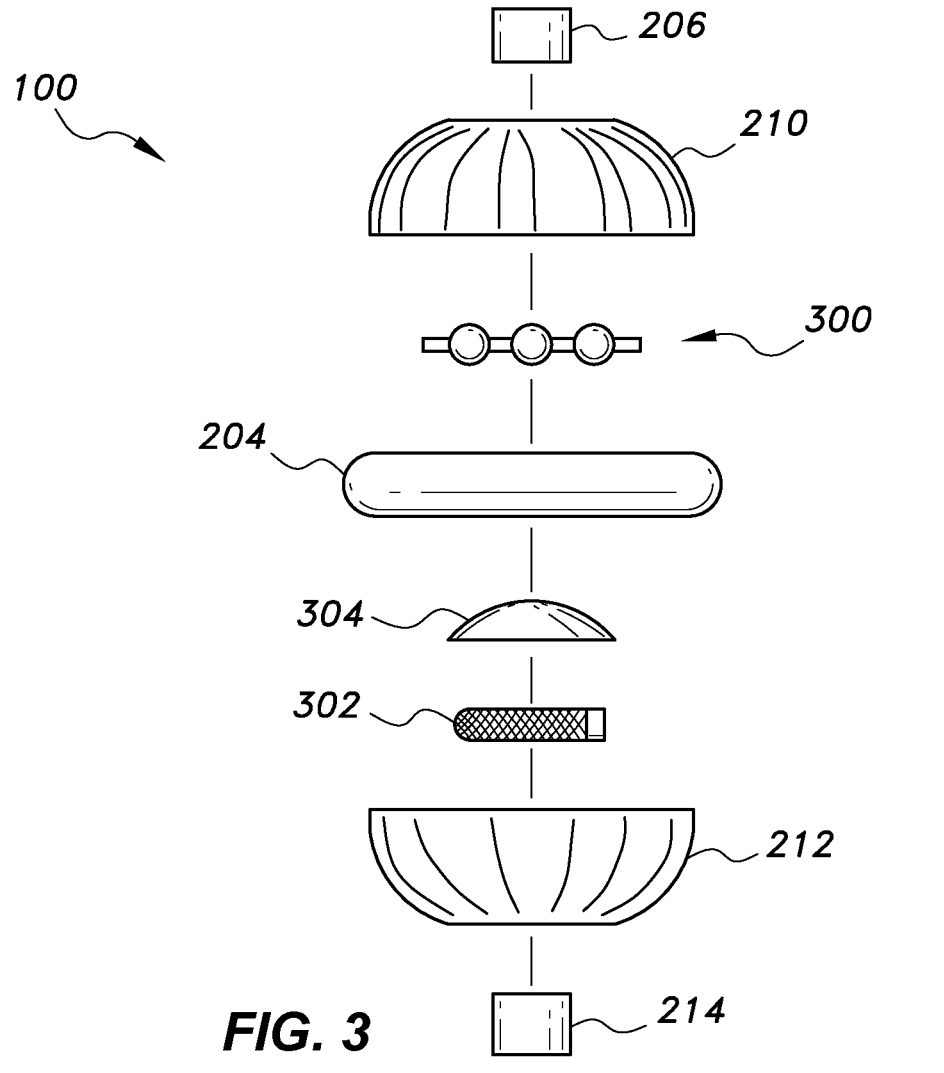
FIG. 3 is an exploded side view of the material detecting device of FIG. 1, showing the internal components of the device.

In an embodiment, a toxic material detecting device 100, shown floating on a body of water W in FIG. 1, allows a quantity of the water W (testing material) to pass therethrough for detecting a toxic material in the body of water W. The toxic material detecting device 100 includes Wi-Fi circuitry as described below for communicating data obtained to a remote device, such as a smartphone SP. A user U operates an application on the smartphone SP that is configured to show, record and retransmit the data received from the material detecting device 100.

Details of a first embodiment of the material detecting device 100 are shown in FIGS. 2-11. The material detecting device 100 can be used in hydrosphere locations, e.g., oceans and rivers, to detect chemical, radioactive, and soil waste, from these locations. A toxic material retaining composition, also referred to herein as "composition h," can retain the toxic material in the water from the hydrosphere locations that passes through the device by adsorption or absorption. The toxic material can be retained for a sufficient time to be detected. An external shell 210, 212 of the device 100 can be made from fiberglass, steel, or other suitable material that can float on water and is capable of withstanding extremely high and low temperatures.

The material detecting device 100 includes a top hemispheric chamber 200, a bottom hemispheric chamber 202, and a perforated central toroid 204. The perforated central toroid 204 includes a plurality of holes 208. A first connector 206 extends through the top hemispheric chamber 200 and a second connector 214 extends through the bottom hemispheric chamber 202. The interior of the material detecting device 100 includes an upper material detecting component 300, a lower material detecting component 302, and a centrally located detecting station 304.

Figure 4:
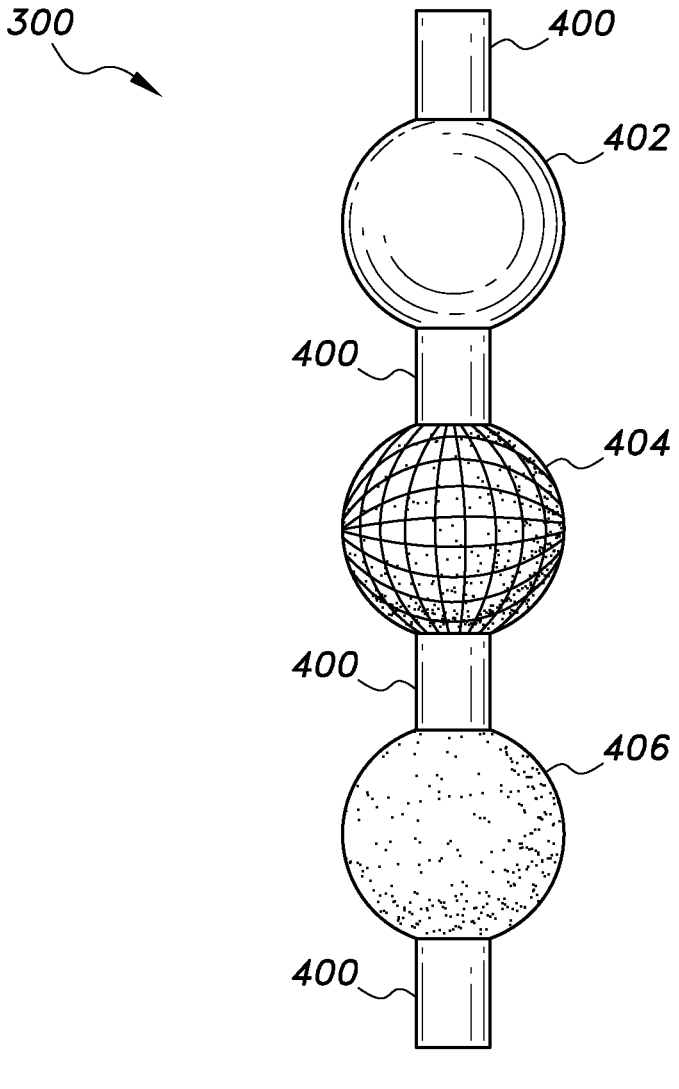
FIG. 4 is a side view of an upper material detecting component of the material detecting device of FIG. 1.
Figure 5:
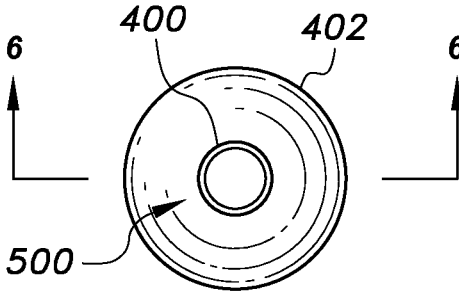
FIG. 5 is a top view of the upper component of FIG. 4.
Figure 6:
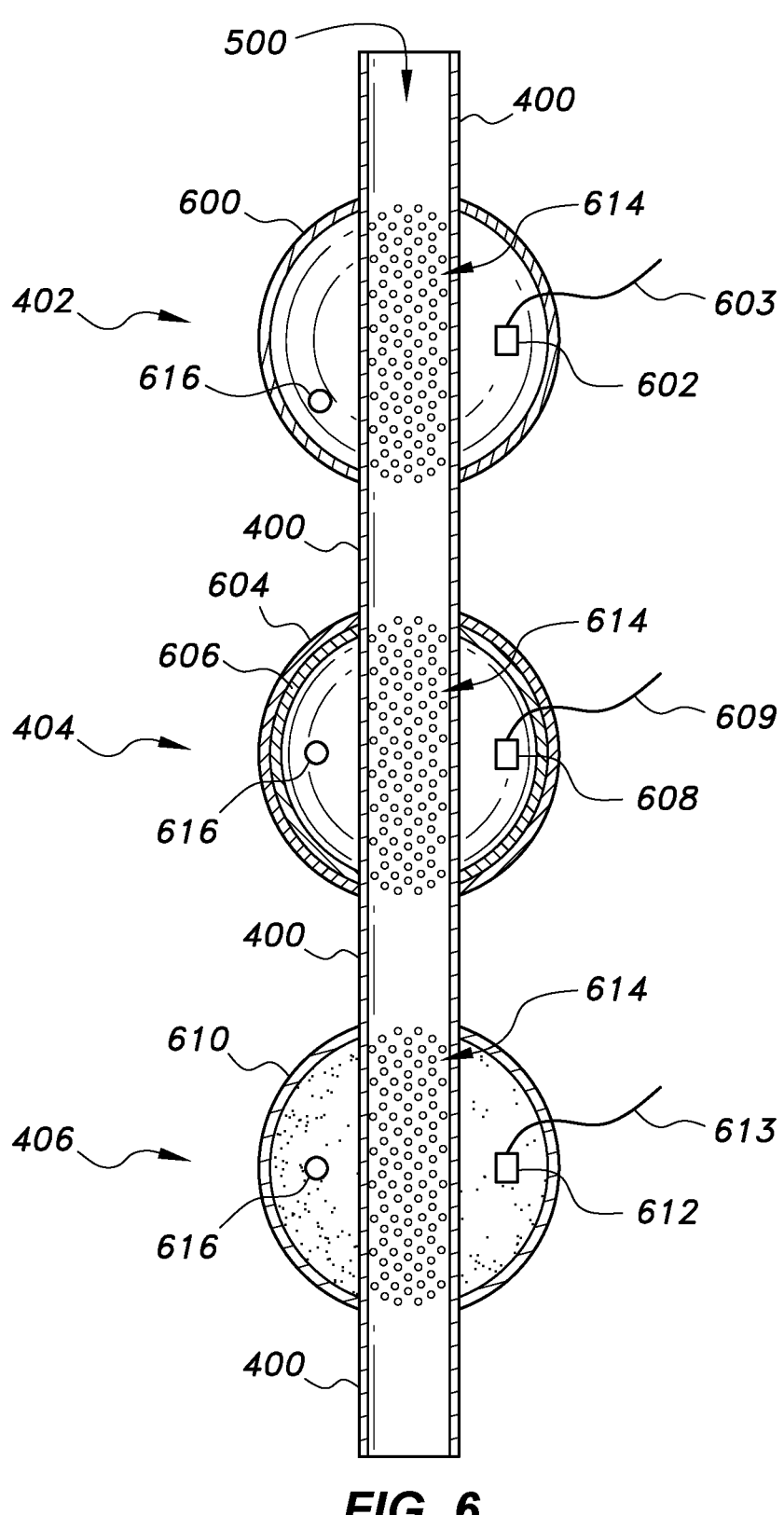
FIG. 6 is a cross-sectional view of the upper component of FIG. 5, taken through line 6-6.

Details of the upper material detecting component 300 are shown in FIGS. 4-6. The upper material detecting component 300 includes a material distribution pipe 400 extending through a first hollow spherical chamber 402, a second hollow spherical chamber 404 and a third hollow spherical chamber 406. The third, hollow spherical chamber 406 can be made from clay, for example clay typically found in Ramadi, Iraq ("Ramadi" clay). The material distribution pipe 400 includes a peripheral wall with a central longitudinal bore 500 extending therethrough and a plurality of perforations 614 defined within the peripheral wall. The material distribution pipe 400 extends through the spherical chambers 402, 404, 406. In the embodiment shown in FIG. 6, the first spherical chamber 402 includes an aluminum shell 600 with a first sensor 602 mounted on an inner surface thereof. First sensor wires 603 connect the first sensor 602 to the detecting station 304. The second spherical chamber 404 includes an inner aluminum shell 606 and on outer graphene coating 604. The graphene coating 604 can have a net-like configuration. The inner aluminum shell 606 has a second sensor 608 mounted on an interior surface thereof. Second sensor wires 609 connect the second sensor 608 to the detecting station 304. The third spherical chamber 406 includes a Ramadi clay shell 610 with a third sensor 612 mounted on an interior surface thereof. The Ramadi clay includes about 69-72% clay, 20-25% silt and a small percentage of trace minerals. The Ramadi clay includes about 70% sodium montmorillonite $(Na, Ca)_{0.33}(Al, Mg)_2(Si_4O_{10})$ $(OH)_2 \cdot nH_2O)$. Sensor wires 603, 609, and 613 connect the sensors 602, 608, and 612, respectively, to the detecting station 304. An interior portion of each of the spherical chambers 402, 404, 406, further includes a toxic material retaining composition 616, as described in detail herein. The sensors 602, 608 and 612 may be gamma radiation, pH, CMOS, gas, temperature, or alpha radiation sensors as described below with respect to FIG. 11.

Figure 7:
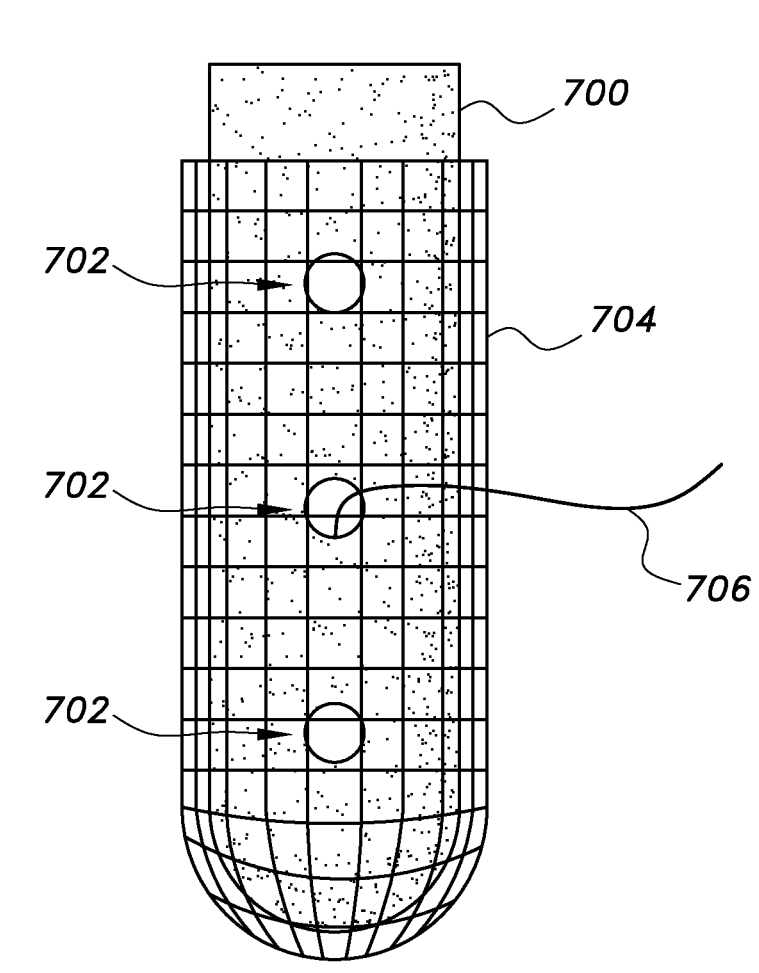
FIG. 7 is a side view of a lower material detecting component of the material detecting device of FIG. 1.
Figure 8:
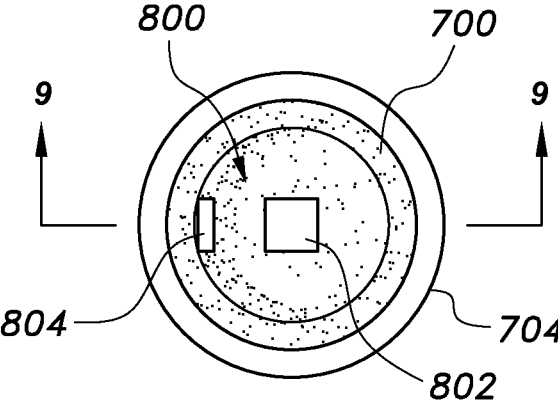
FIG. 8 is a top view of the lower component of FIG. 7.
Figure 9:
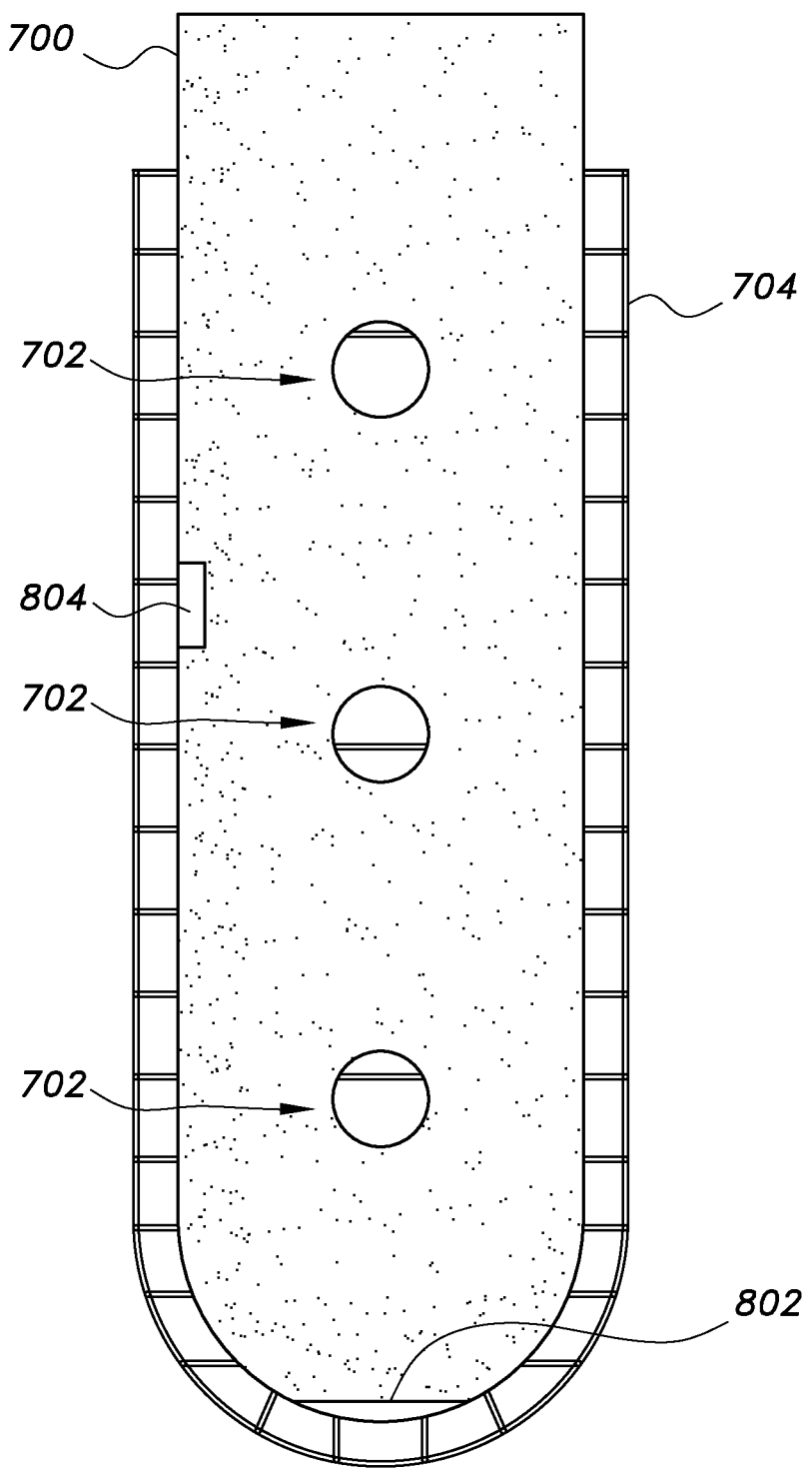
FIG. 9 is a cross-sectional view of the lower component of FIG. 8, taken through line 9-9.

Details of the lower material detecting component 302 are shown in FIGS. 7-9. The lower material detecting component 302 includes an inner clay cylinder 700 and an outer graphene netting 704. The inner clay cylinder 700 includes a peripheral wall having a central blind bore 800 extending therethrough and a plurality of holes 702 defined within the wall. A fourth sensor 804 is mounted on an interior of the peripheral wall of the inner clay cylinder 700 and sensor wires 706 extend through one of the holes 702. A toxin retaining composition 802 is disposed at a bottom of the blind bore 800. The sensor 804 may be a radiation, pH, CMOS, gas, temperature, or alpha radiation sensor as described below with respect to FIG. 11.

Figure 10:
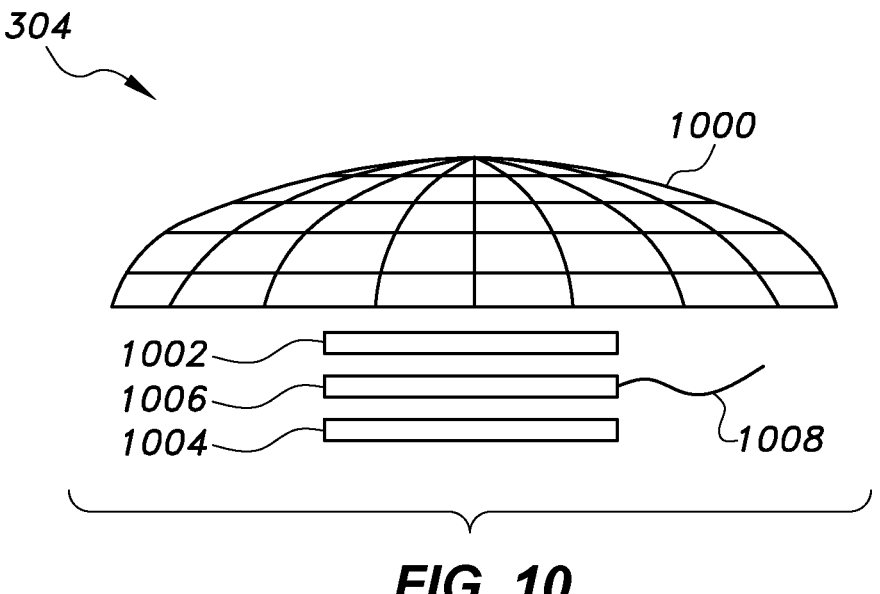
FIG. 10 is an exploded side view of a centrally located signal processing and communication station of the material detecting device of FIG. 1.
Figure 12:
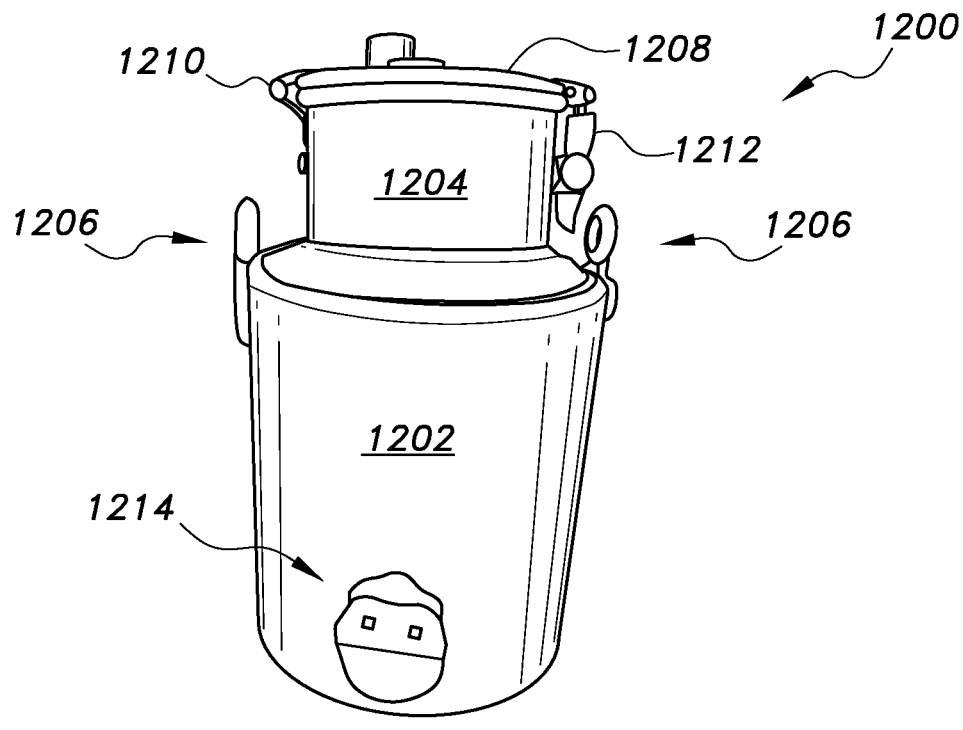
FIG. 12 is a side view of a second embodiment of a toxic material detecting device.

Details of the detecting station 304 are shown in FIG. 10. The station 304 includes a wire support shell 1000, an upper half of a waterproof container 1002, a lower half of waterproof container 1004, and a printed circuit board (PCB) 1006. The upper half of the waterproof container 1002 and the lower half of the waterproof container 1004 are sealed together with the PCB 1006 therein, to protect PCB 1006 from the material. A wiring harness 1008 connects the PCB 1006 to the sensors 602, 608, 612, 804 and includes sensor wires 603, 608, 612, 706.

A circuit diagram 1100 of the material detecting device 100 is shown in FIG. 11. The circuit includes a microcontroller 1102, such as an Arduino/Genuino Uno and an analog multiplexor 1104 such as a CD4051BE, produced by various manufacturers. A communication module 1112, such as Bluetooth Arduino model HC-05, provides communication with a smartphone SP as shown in FIG. 1, or other devices. Other communication protocols/devices such as Wi-Fi may be used, or the data may be stored in the memory of the microcontroller and downloaded when the material detecting device 100 is retrieved. The microcontroller 1102, the multiplexor 1104 and the Bluetooth module 1112 are centrally located on the PCB 1006 or on multiple circuit boards within the sealed waterproof container halves 1002, 1004. The circuit diagram 1100 also includes various sensors which may be centrally located or may be any of the sensors described with respect to the embodiments of the material detecting device described herein. The sensors include a gamma radiation detector 1106, such as an X100-7 photodiode; a pH sensor 1108, such as the Gravity analog pH sensor/meter pro kit for Arduino; a CMOS image sensor 1110, such as the OV7670 camera module; an air quality sensor 1114, such as a BME680 MEMS gas, humidity, pressure and temperature sensor; an analog temperature sensor 1116, such as an LM35 from Texas Instruments; and an alpha radiation sensor 1118. The power for the various components can be provided by a rechargeable battery (not shown).

Figure 13:
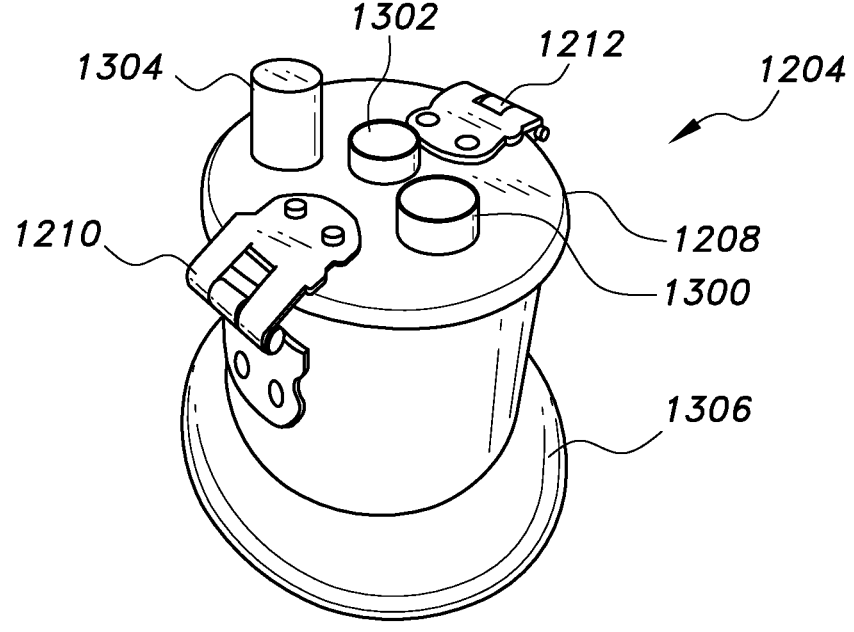
FIG. 13 is an isometric top view of an upper chamber of the material detecting device of FIG. 12.

A second embodiment of a toxic material detecting device 1200 is shown in FIGS. 12-20. The toxic material detecting device 1200 can be used for petroleum (oil) production and hydraulic fracturing for gas production. A first portion of the toxic material detecting device includes a lower main chamber 1202, an upper chamber 1204, and latches 1206 for sealing the upper chamber 1204 to the lower chamber 1202. A lid 1208 is attached to the open top of the upper chamber 1204 by a hinge 1210 and a latch 1212 that is provided to maintain the lid 1208 in a closed position. An electrical input connector 1214 is connected to an electrical source (not shown) for powering the internal components. As is best seen in FIG. 13, an input pipe 1300 extends into the interior of the upper chamber 1204, a material distribution pipe 1302, and a thermometer 1304 extend through the openings in the lid 1208. Also as best seen in FIG. 13, the upper chamber 1204 includes a lower slanted flange 1306 for engagement by the latches 1206.

Figure 14:
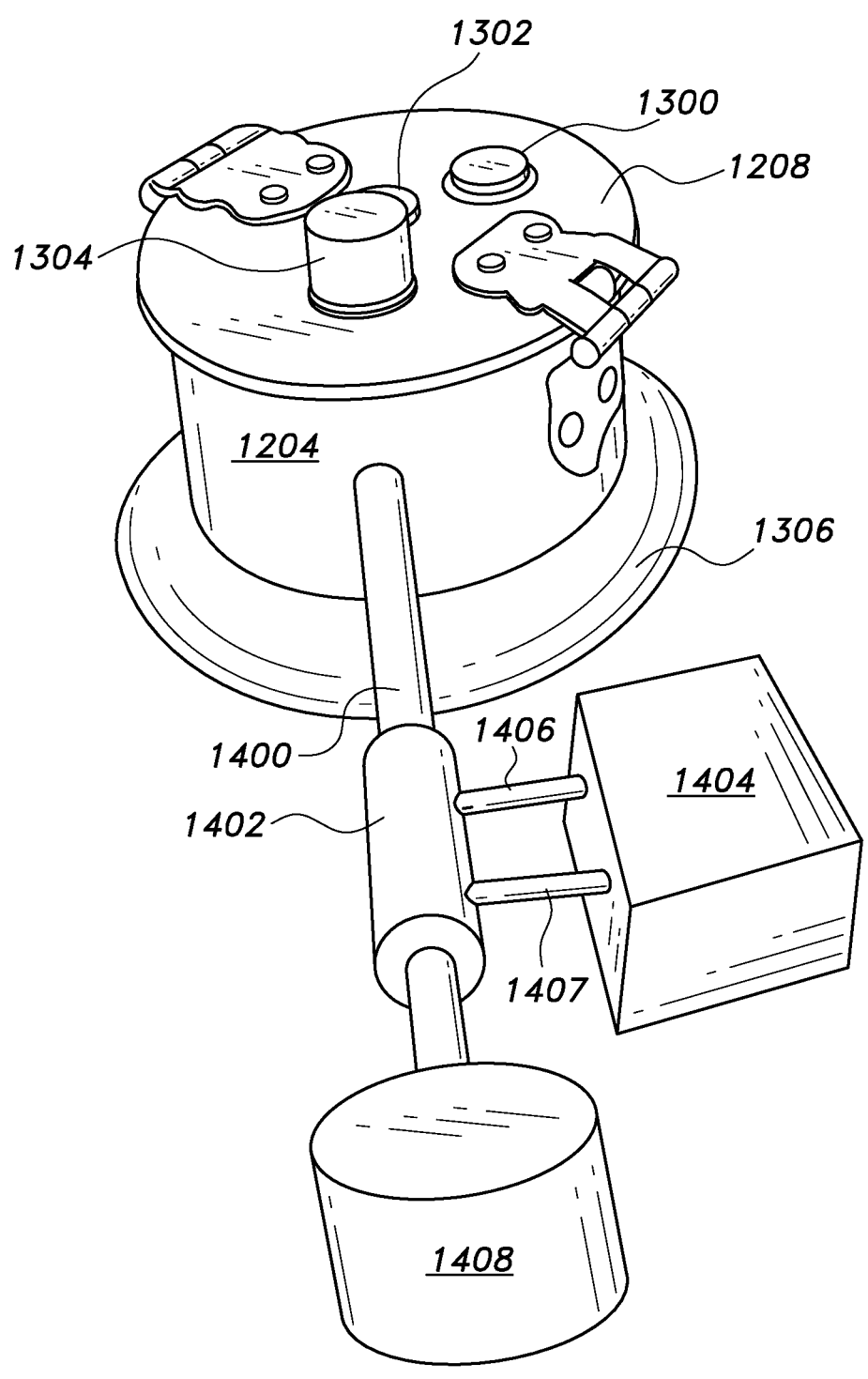
FIG. 14 is an isometric top view of the upper chamber of FIG. 13, showing it connected to external distillation equipment.
Figure 15:
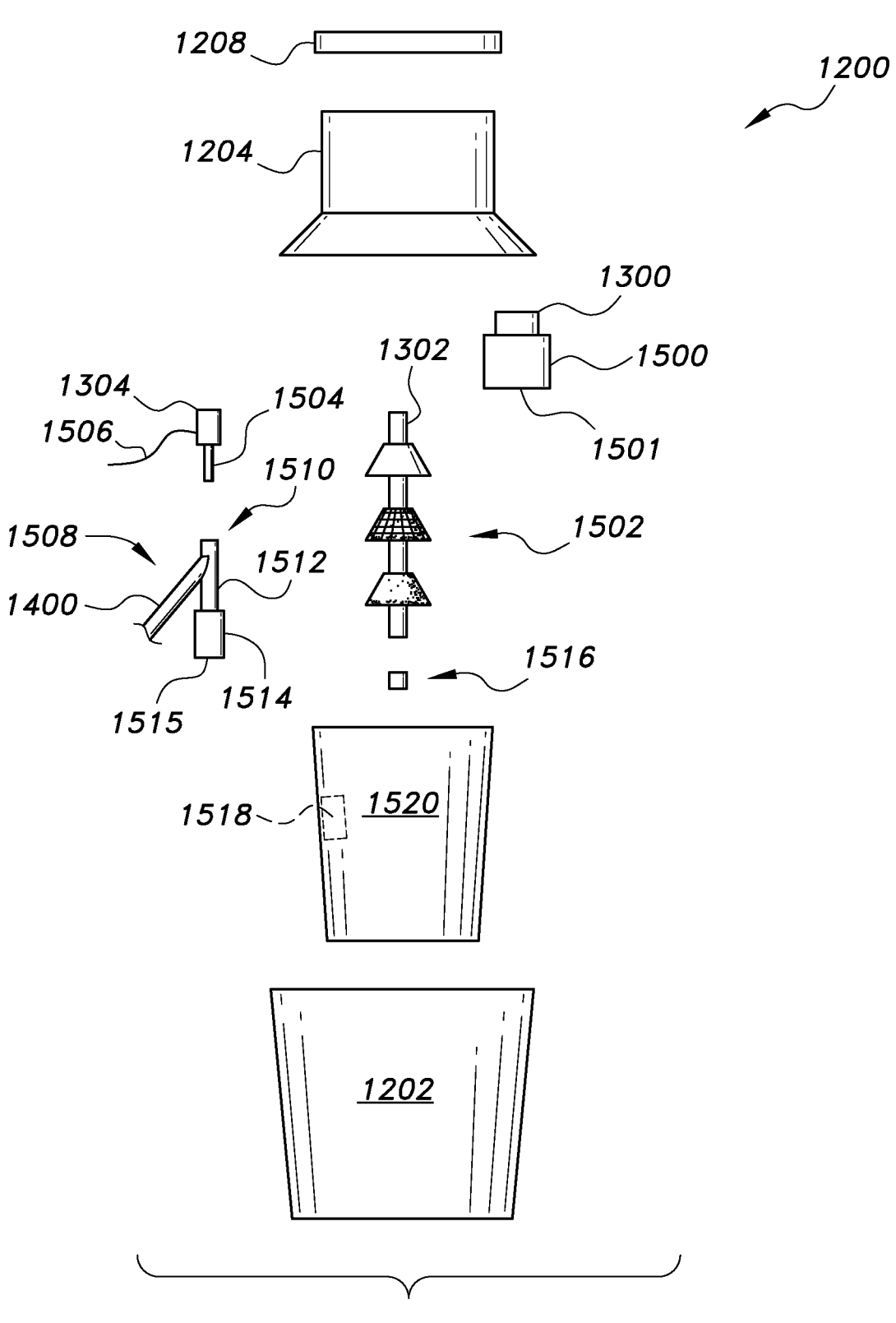
FIG. 15 is an exploded side view of the material detecting device of FIG. 12, showing the internal components thereof.
Figure 16:
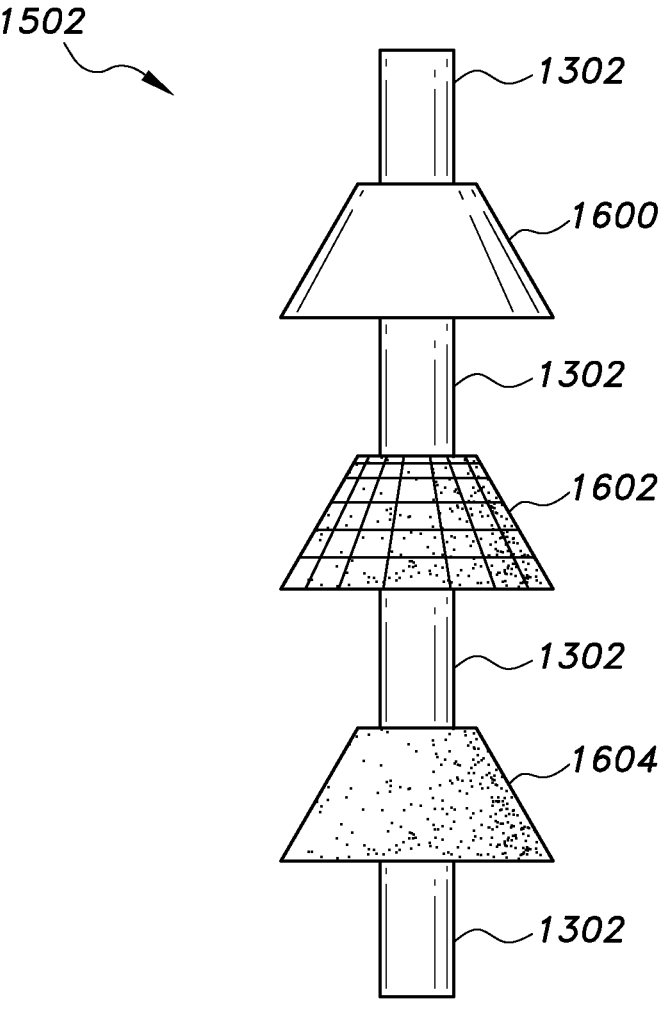
FIG. 16 is a side view of a material detecting component of the material detecting device of FIG. 12.
Figure 17:
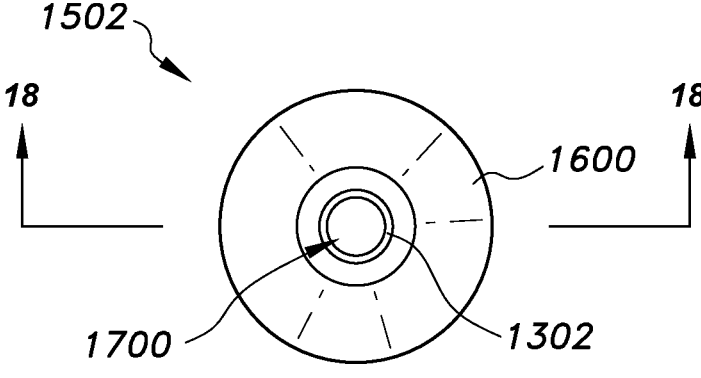
FIG. 17 is a top view of the material detecting component of FIG. 16.

FIG. 14 shows the material detecting device 1200 connected to external distillation equipment. A condenser supply pipe 1400 extends through a hole in the sidewall of the upper chamber 1204 and through a cooling jacket 1402. A chiller 1404 supplies cold coolant to the cooling jacket 1402, via a cold coolant supply pipe 1406, and receives warm coolant from the cooling jacket 1402, via a warm coolant return line 1407. Condensate from the condenser supply pipe 1400 is received in a condensate vessel 1408.

Details of the internal components of the material detecting device 1200 are shown in FIGS. 15-20. The input pipe 1300 is connected to an inlet plenum 1500, with a bottom wall 1501 having a plurality of perforations 2000 (FIG. 20) for distributing the material being tested into the interior of the material detecting device 1200. The material distribution pipe 1302 is part of a material detection component 1502, which is described in detail below with respect to FIGS. 16-18. The thermometer 1304 includes a temperature probe

1504 and wires 1506, for connecting the thermometer 1304 to a microcontroller of the material detecting device 1200. A condenser supply assembly 1508 includes a thermometer probe port 1510 at the top end of a device outlet pipe 1512. The condenser supply pipe 1400 extends downwardly from the device outlet pipe 1512. An outlet plenum 1514 supplies the testing material to the device outlet pipe 1512. The bottom wall 1515 of the outlet plenum 1514 includes a plurality of perforations 1900 (FIG. 1). A waterproof circuit board housing 1516 is located at the bottom of the device 1200 and houses a PCB such as the PCB 1006 described with respect to device 100. A sensor 1518 is located near the bottom of the device 1200 and is attached to a sidewall of a clay vessel or liner 1520 that is disposed in the lower chamber 1202. The sensor 1518 is connected to the PCB via the wiring harness. The lower main chamber 1202 may be heated by an external or internal heater connected to the liner 1520, thereby forming a clay-lined oven.

The clay liner 1520 may be formed from Ramadi clay. In an embodiment, the clay liner 1520 can be prepared by: washing Ramadi clay with distilled water using a sieving method or any other suitable method; pouring 0.3 grams of poly(3-aminopropyl) siloxane hydrochloride (PAPS-Cl) in 20 ml distilled water into an aqueous suspension of Ramadi clay containing 70% saturated Na+-montmorillonite (0.3 g Na− MMT/20 mL—distilled water); mixing and stirring the solution for up to 2 hours at 80° C. to get a cross-linked product of PAPS-MMT; increasing the temperature to 100° C. to form an intercalated nanocomposite of PAPS-MMT; adding graphene oxide (0.3 g/250 ml in) to PAPS-MMT and stirring for 5 hours under 80° C.; raising the temperature up to 200° C. for two hours; and gradually increasing the temperature from 200° C.-500° C. for another 4 hours.

Figure 18:
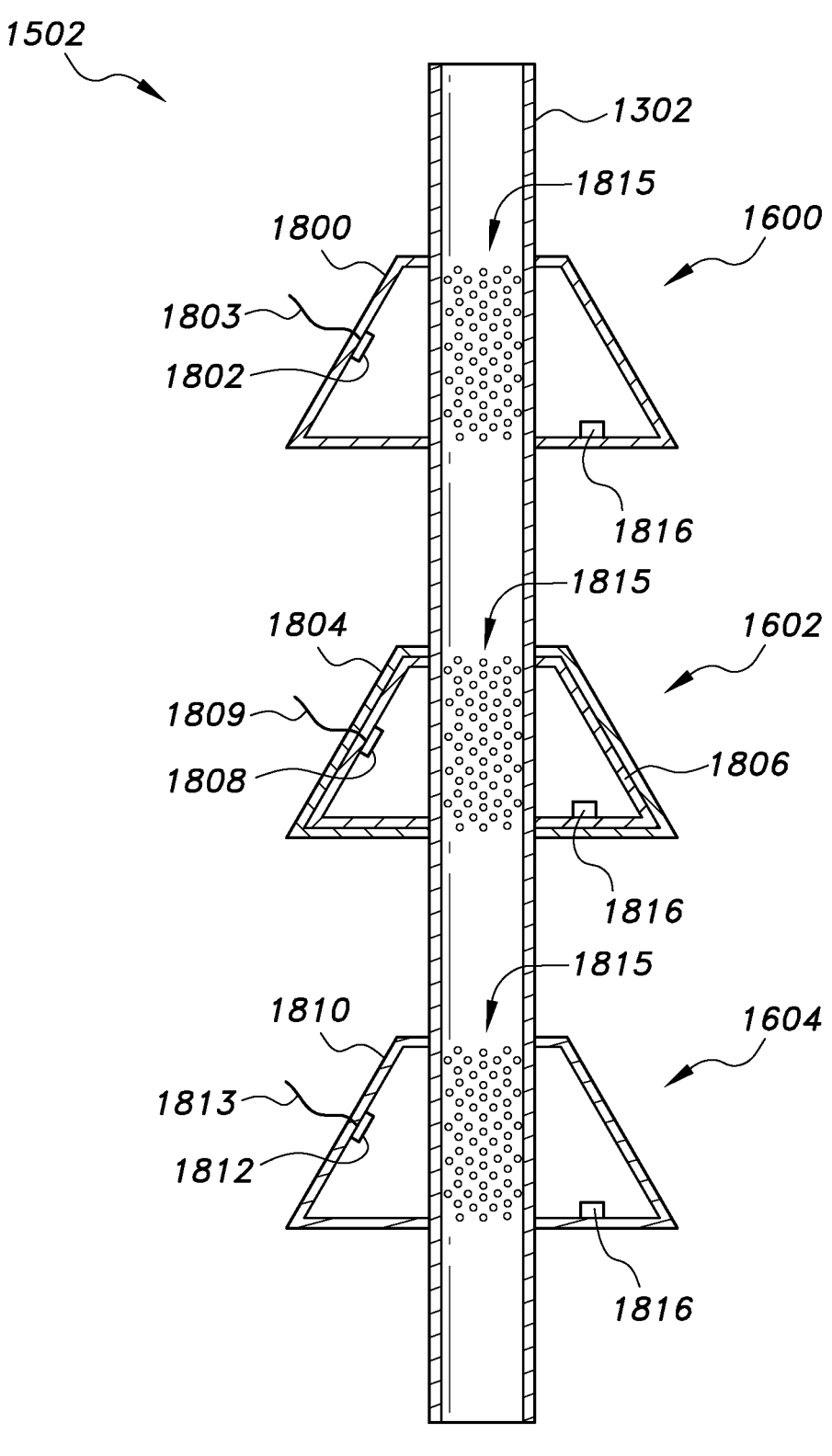
FIG. 18 is a cross-sectional view of the material detecting component of FIG. 17, taken through line 18-18.
Figure 19:
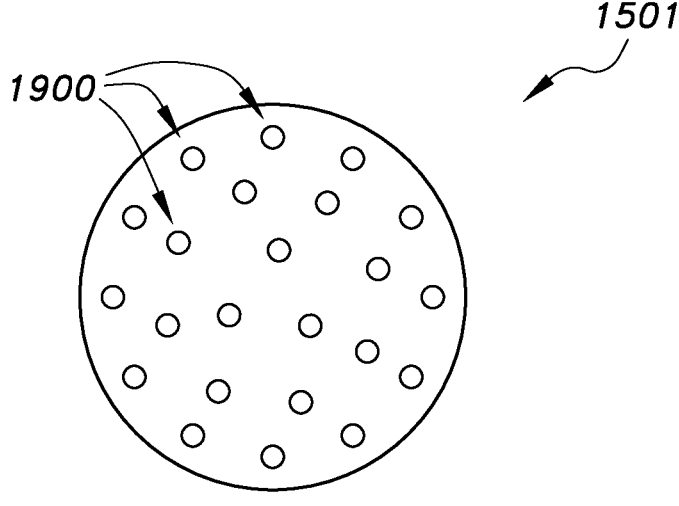
FIG. 19 is a bottom view of an outlet plenum of the material detecting device of FIG. 12.
Figure 20:
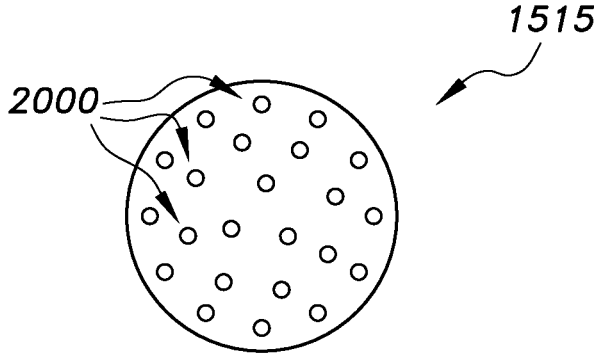
FIG. 20 is a bottom view of an inlet plenum of the material detecting device of FIG. 12.

The material detection component 1502 includes the material distribution pipe 1302, a first hollow frustoconical chamber 1600, a second hollow frustoconical chamber 1602, and a third hollow frustoconical chamber 1604. The first hollow frustoconical chamber 1600 can be made from aluminum. The second hollow frustoconical chamber 1602 can have an aluminum shell and a graphene coating. The third hollow frustoconical chamber 1604 can be made from clay, e.g., Ramadi clay. The material distribution pipe 1302 includes a peripheral wall with a central longitudinal bore 1700 extending therethrough. A plurality of perforations 1815 are defined within the peripheral wall to allow material to pass from the bore 1700 into the frustoconical chambers 1600, 1602, 1604. As best seen in FIG. 18, the first frustoconical chamber 1600 includes an aluminum shell 1800 with a first sensor 1802 mounted on an interior surface thereof. First sensor wires 1803 connect the first sensor 1802 to the PCB in the waterproof circuit board housing 1516. The second frustoconical chamber includes an outer graphene coating 1804 on an inner aluminum shell 1806. The inner aluminum shell 1806 has a second sensor 1808 mounted on an interior surface thereof. Second sensor wires 1809 connect the second sensor 1808 to the PCB in the waterproof circuit board housing 1516. The third frustoconical chamber 1604 includes a Ramadi clay shell 1810 and a third sensor 1812 mounted on an interior surface thereof. Third sensor wires 1813 connect the third sensor 1812 to the PCB in the waterproof circuit board housing 1516. The interior of each of the frustoconical chambers 1600, 1602, 1604, further includes the toxic material retaining composition 1816 described below. The sensors 1802, 1808 and 812 may be radiation, pH, CMOS, gas, temperature, or alpha radiation sensors as described above with respect to FIG. 11.

The toxic material retaining composition for use in conjunction with the above material detecting devices includes a montmorillonite/poly(vinyl alcohol) (MMT/PVA) zeolite/activated charcoal composite (MMT-MMT-PVA-MMT-NZC-MMT), with cocamidopropyl betaine (CAPB) positioned between the central portions of the MMT layers and sodium lauryl ether sulfate (SLES) positioned between the edge portions of the MMT layers. The toxic material retaining composition or "composition (h)" can be highly adsorbent and has high porosity.

An exemplary method for making composition (h) can include: mixing and grinding 1 gram of Zeolite with pore diameters between 0.3 and 0.6 nm, (NZ) and 0.3 gram of activated charcoal (AC) in a crucible; placing the mixture into a two liter flask and adding 500 ml of distilled water; stirring the solution with a magnetic stirrer and heating to 80° C. for one hour, thereby forming mixture (a) (NZ-AC); mixing polyvinyl acetate (PVAC) and sodium tetraborate (STB) in the presence of sodium hydroxide and stirring for two hours under 80° C. to form mixture (b) (cross-link of polyvinyl borate PVA-B-PVA); pouring mixture (b) into mixture (a) and maintaining a temperature of 90° C. for two hours to form adsorbent product (c) (PVA-NZ-AC); washing Ramadi clay (tiny grain (0.001-0.002 mm) which includes 70% sodium montmorillonite $(Na, Ca)_{0.33}(Al, Mg)_2(Si_4O_{10})$ $(OH)_2$ $nH_2O$) using a sieving method or any other appropriate method; pouring 0.3 grams of poly(3-aminopropyl) siloxane hydrochloride (PAPS-Cl) into 20 ml distilled water into an aqueous suspension of the Ramadi clay; mixing and stirring the solution for up to 2 hours at 80° C. to get a product of cross-linked PAPS-MMT; increasing the temperature of the solution to 100° C. for an hour to form mixture (d) (an intercalated nanocomposite of PAPS-MMT); pouring product (c) into mixture (d) with a few drops of NaOH for two hours under 80° C. to form product (e); adding 20% of Cocamidopropyl betaine (CAPB—$C_{19}H_{38}N_2O_3$) to 20% of product (e) with 60% distilled water in a glass container in the presence of hydrochloric acid (HCL); stirring under 80° C. for an hour to allow the cation exchange procedure to take place in between MMT interlayers and at the edge of MMT layers, thereby forming product (f); adding 3 grams of sodium lauryl ether sulfate (SLES—$CH_3(CH_2)_{11}(OCH_2CH_2)_nOSO_3Na$) into a lab flux containing one liter of degassed water and heating to 50° C.; stirring the mixture until the product gets viscous, thereby forming mixture (g); pouring 10% of mixture (g) into 30% of product (f) with 60% distilled water; and stirring the mixture for two hours at 80° C. to produce composition (h). In the composition (h), the SLES is bound inside the MMT layers and increases the clay's water affinity.

It is to be understood that the toxic material detecting device is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A toxic material detecting device comprising:
   a detecting station having a circuit board with a microcontroller;
   a first material detecting chamber having an aluminum shell, a first sensor on an inner surface of the aluminum shell, and a toxic material retaining composition within the aluminum shell of the first material detecting chamber;

a second material detecting chamber having an aluminum shell and an outer graphene coating on the aluminum shell, a second sensor on an inner surface of the aluminum shell, and a toxic material retaining composition within the aluminum shell of the second material detecting chamber;

a third material detecting chamber having a clay shell, a third sensor on an inner surface of the clay shell, and a toxic material retaining composition within the clay shell of the third material detecting chamber;

a material distribution pipe extending through the material detecting chambers, the material distribution pipe having a central through bore and a plurality of perforations in a peripheral wall thereof; and a wiring harness connecting the circuit board to the first, second and third sensors.

2. The material detecting device as recited in claim 1, wherein the detecting station includes a communication module for transmitting data from the first, second and third sensors to a remote device.

3. The material detecting device as recited in claim 1, wherein the microcontroller includes memory for storing data from the first, second and third sensors.

4. The material detecting device as recited in claim 1, wherein the first, second and third sensors are selected from the group consisting of gamma radiation sensors, pH sensors, CMOS image sensors, gas sensors, temperature sensors and alpha radiation sensors.

5. The material detecting device as recited in claim 1, wherein the shells of the first, second and third detection chambers have a shape selected from the group consisting of spherical and frustoconical.

6. The material detecting device as recited in claim 1, further comprising:

at least one device chamber, the at least one device chamber comprising an upper chamber and a lower chamber, a first material detecting component being in the upper chamber, and a second material detecting device being in the lower chamber.

7. The material detecting device as recited in claim 6, wherein the second material detecting component comprises:

an inner hollow cylindrical compartment having a peripheral wall, a central blind bore extending along a length of the peripheral wall, and a plurality of holes defined through the peripheral wall;

an outer graphene coating surrounding the inner hollow cylindrical compartment;

a fourth sensor mounted on an inner surface of the peripheral wall;

a toxic material retaining composition within the cylindrical compartment; and a wiring harness connecting the circuit board to the fourth sensor.

8. The material detecting device as recited in claim 7, wherein the first, second, third and fourth sensors are chosen from the group consisting of gamma radiation sensors, pH sensors, CMOS image sensors, gas sensors, temperature sensors and alpha radiation sensors.

9. The material detecting device as recited in claim 8, wherein the detecting station includes a communication module for transmitting data from the first, second, third and fourth sensors to a remote device.

10. The material detecting device as recited in claim 8, wherein the microcontroller includes memory for storing data from the first, second, third and fourth sensors.

11. The material detecting device as recited in claim 8, wherein the first, second and third detection chambers are spherical in shape.

12. The material detecting device as recited in claim 1, further comprising:

at least one device chamber comprising an upper chamber and a lower chamber, the upper chamber has a sidewall, an open top and a lid attached to and covering the open top of the upper chamber, the lid includes a first opening therethrough, and a first end of the material distribution pipe extending through the first opening and a second end of the material distribution pipe extends into the lower main chamber.

13. The material detecting device as recited in claim 12, wherein the lid includes second and third opening therethrough and the material detecting device further comprises:

a device inlet plenum attached to the second end of the device input pipe, the device inlet plenum having a bottom wall with a plurality of perforations;

a condenser supply pipe attached to and extending through a hole in the sidewall of the upper chamber; and a device outlet plenum attached to the second end of the device outlet pipe, the device outlet plenum having a bottom wall with a plurality of perforations.

14. The material detecting device as recited in claim 13, wherein:

the first end of the device outlet pipe has a thermometer probe port; and the material detecting device includes a thermometer with a temperature probe extending through the thermometer probe port; and the wiring harness connects the thermometer to the circuit board.

15. The material detecting device as recited in claim 12, further comprising:

a clay liner in the lower chamber, the clay liner having a bottom surface and a peripheral wall extending upright from the bottom surface;

a fourth sensor attached to an inner surface of the peripheral wall of the clay liner, wherein: the wiring harness connects the fourth sensor to the circuit board; and the first, second, third and fourth sensors are chosen from the group consisting of gamma radiation sensors, pH sensors, CMOS image sensors, gas sensors, temperature sensors and alpha radiation sensors.

16. The material detecting device as recited in claim 1, wherein the adsorbent composition is a layered composite comprising: montmorillonite; poly (vinyl alcohol); zeolite; activated charcoal; cocamidopropyl betaine; and sodium lauryl ether sulfate positioned.

17. The material detecting device as recited in claim 16, wherein the toxic material retaining composition comprises a montmorillonite/poly (vinyl alcohol) zeolite/activated charcoal layered composite.

18. A method of making the toxic material retaining composition of claim 1, comprising the steps of:

mixing and grinding zeolite with activated charcoal;

adding distilled water to the zeolite and activated charcoal mixture;

stirring and heating the solution thereby forming a mixture (a);

mixing polyvinyl acetate and sodium tetraborate in the presence of sodium hydroxide and stirring to form a mixture (b);

pouring mixture (b) into mixture (a) to form an adsorbent product (c);

providing a clay having 70% sodium montmorillonite;

pouring poly (3-aminopropyl) siloxane hydrochloride in distilled water into an aqueous suspension of the clay;

mixing and stirring the solution to get a product of cross-linked PAPS-MMT;

increasing the temperature of the solution to form a mixture (d);

pouring product (c) into mixture (d) with a few drops of NaOH to form a product (e);

adding cocamidopropyl betaine to product (e) with distilled water in the presence of hydrochloric acid;

stirring the solution to form product (f);

adding sodium lauryl ether sulfate to degassed water and heating;

stirring the mixture until the product gets viscous, thereby forming a mixture (g);

pouring mixture (g) into product (f) with distilled water; and stirring the mixture to produce the adsorbent composition.

* * * * *